(12) United States Patent
Van Buskirk et al.

(10) Patent No.: US 6,316,797 B1
(45) Date of Patent: Nov. 13, 2001

(54) SCALABLE LEAD ZIRCONIUM TITANATE (PZT) THIN FILM MATERIAL AND DEPOSITION METHOD, AND FERROELECTRIC MEMORY DEVICE STRUCTURES COMPRISING SUCH THIN FILM MATERIAL

(75) Inventors: Peter C. Van Buskirk, Newtown; Jeffrey F. Roeder, Brookfield; Steven M. Bilodeau, Oxford; Michael W. Russell, Nowalk; Stephen T. Johnston, Bethel; Daniel J. Vestyck, Danbury; Thomas H. Baum, Fairfield, all of CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 09/251,890

(22) Filed: Feb. 19, 1999

(51) Int. Cl.[7] .................... H01L 29/76; H01L 29/94; H01L 31/062; H01L 31/113; H01L 31/119

(52) U.S. Cl. ................ 257/295; 257/310; 438/3; 361/311; 361/321.5

(58) Field of Search .............. 106/287.18; 257/295, 257/310; 438/3; 117/104; 361/311, 321.1, 321.4, 321.5

(56) References Cited

U.S. PATENT DOCUMENTS

| | | | |
|---|---|---|---|
| 5,407,855 | * 4/1995 | Maniar et al. | 438/3 |
| 5,555,486 | * 9/1996 | Kingon et al. | 361/305 |
| 5,572,052 | 11/1996 | Kashihara et al. | 257/295 |
| 5,644,184 | 7/1997 | Kucherov | 310/306 |
| 5,757,061 | 5/1998 | Satoh et al. | 428/220 |
| 5,846,275 | 12/1998 | Lane et al. | 55/431 |
| 5,913,117 | * 6/1999 | Lee | 438/240 |
| 5,916,359 | * 6/1999 | Baum et al. | 106/287.18 |
| 6,165,804 | * 12/2000 | Fazan et al. | 438/3 |
| 6,198,119 | * 3/2001 | Nabatame et al. | 257/295 |

OTHER PUBLICATIONS

P.K. Larsen et al., "Nanosecond swithching of thin ferroelectric films" Applied Physics Letters. vol. 59, Issue 5, pp. 611–613 (1991).

(List continued on next page.)

Primary Examiner—Carl Whitehead, Jr.
Assistant Examiner—Jamie L. Brophy
(74) Attorney, Agent, or Firm—Robert A. McLauchlan, III; Oliver A. Zitzmann; Steven J. Hurltquist

(57) ABSTRACT

A novel lead zirconium titanate (PZT) material having unique properties and application for PZT thin film capacitors and ferroelectric capacitor structures, e.g., FeRAMs, employing such thin film material. The PZT material is scalable, being dimensionally scalable, pulse length scalable and/or E-field scalable in character, and is useful for ferroelectric capacitors over a wide range of thicknesses, e.g., from about 20 nanometers to about 150 nanometers, and a range of lateral dimensions extending to as low as 0.15 $\mu$m. Corresponding capacitor areas (i.e., lateral scaling) in a preferred embodiment are in the range of from about $10^4$ to about $10^{-2}$ $\mu m^2$. The scalable PZT material of the invention may be formed by liquid delivery MOCVD, without PZT film modification techniques such as acceptor doping or use of film modifiers (e.g., Nb, Ta, La, Sr, Ca and the like).

37 Claims, 7 Drawing Sheets

OTHER PUBLICATIONS

J. F. Roeder et al., "Liquid Delivery MOCVD of Ferroelectric PZT", Mat. Res. Symp. Proc., vol. 415, (1996) pp. 123–128.

P.K. Larsen et al., "Ferroelectric properties and fatigue of $PbZr_{0.51}Ti_{0.49}O_3$ thin films of varying thickness: blocking layer model" Appl. Phys. vol. 76 Issue 4, (1994) pp. 2405–2413.

A. K. Tagantsev et al., "Depletion and depolarization effects in ferroelectric thin films and their manifestations in switching and fatigue", Integrated Ferroelectrics, vol. 6, (1994) pp. 309–20.

A. K. Tagantsev et al, Integrated Ferroelectrics, vol. 4, Issue 1. (1994).

M. De Keijser et al., "Organometallic chemical vapor deposition of lead zirconate–titanate thin films" Mat. Res. Symp. Proc., vol. 310, (1993) pp. 223–234.

K.H. Hartl and H. Rau, "PbO Vapour Pressure in the $Pb(Ti_{1-x}Zr_x)O_3$ System" Solid State Comm., vol. 7, Issue 41 (1969).

* cited by examiner

SCALABLE LEAD ZIRCONIUM TITANATE (PZT) THIN FILM MATERIAL AND DEPOSITION METHOD, AND FERROELECTRIC MEMORY DEVICE STRUCTURES COMPRISING SUCH THIN FILM MATERIAL

BACKGROUND OF THE INVENTION

1. Field of the Invention

This invention relates generally to a novel lead zirconium titanate (PZT) material having unique properties and application for PZT thin film capacitors, as well as to a deposition method for forming PZT films of such material, and ferroelectric capacitor structures employing such thin film material.

2. Description of the Related Art

There is a major effort by semiconductor companies throughout the world to commercialize high dielectric constant and ferroelectric thin films in advanced dynamic random access memories (DRAMs) and ferroelectric random access memories (FeRAMs), respectively.

While the majority of current efforts are directed to the commercial development of relatively large capacitors (e.g. 5 $\mu m^2$ area), the ultimate goal is to adapt ferroelectric random access memory technology for future generations of integrated circuit devices in which capacitor areas, cell sizes and operating voltages are scaled downward as the technology evolves.

For FeRAM devices, most research is currently being directed to either ferroelectric $SrBi_2Ta_2O_9$ (SBT) or $Pb(Zr, Ti)O_3$ (PZT) thin films. Each material has relative advantages and disadvantages. Pt/SBT/Pt capacitors, for example, have been shown to have excellent fatigue and retention characteristics, although processing temperatures in excess of 750° C. pose integration issues. For PZT, phase-pure thin films can be deposited at temperatures in the 450–650° C. range, although Pt/PZT/Pt capacitors are known to suffer from poor fatigue and retention. In the prior art usage of previously known PZT materials, doping and/or oxide electrodes have been needed to produce satisfactory capacitor electrical properties.

Much of the previous work in the field that has established the feasibility of PZT and SBT for memory applications has focused on films that switch at 3V and above. Given the inexorable trends towards smaller circuit elements and lower operating voltages, it is extremely desirable to achieve high reliability and performance for thin films at low operating voltages, especially below 2V.

Low operating voltage requires a combination of adequately low coercive field ($E_c$) and film thickness. SBT films have been shown to have low $E_c$ ($\approx 35$ kV/cm) at thicknesses on the order of 140 nm, resulting in coercive voltages of 0.5V. SBT, however, is handicapped by a low value of switched ferroelectric polarization ($P_{sw}$), typically less than 25 $\mu C/cm^2$. Furthermore, the thermal processing (800° C.) required for improvement of thin film properties is considered severe and undesirable.

Several studies have presented thickness scaling data for PZT films as thin as ~150 nm. See, for example, P. K. Larsen, G. J. M. Dormans, and P. J. Veldhoven, J. Appl. Phys., 76, (4), 1994; and A. K. Tagantsev, C. Pawlaczyk, K. Brooks, and N. Setter, Integrated Ferroelectrics, 4, (1), 1994. These studies have shown that as the film thickness is reduced, the coercive field increases and the polarization decreases. Such effects have been attributed to depletion and depolarizing phenomena (A. K. Tagantsev, C. Pawlaczyk, K. Brooks, M. Landivar, E. Colla and N. Setter, Integrated Ferroelectrics, 6, 309 (1995)).

The foregoing effects have been considered by the art to be intrinsic to thin film PZT, and thus low voltage and thickness scaling of PZT was discouraged.

The high ferroelectric polarization and low processing temperatures of PZT (compared to other materials) provide a compelling motivation to identify a form of PZT and a deposition process that allows scaling the material to low operating voltages.

It would therefore be a major advance in the art, and accordingly is an object of the present invention, to provide a form of PZT and a deposition process that allows scaling of the PZT material to low operating voltages.

It is another object of the invention to provide a PZT material that is scalable in lateral dimensions (i.e. dimensions parallel to the film surface) without incorporating in the material acceptor dopants or modifiers, e.g., Nb, Ta, La, Sr, Ca, etc.

It is a further object of the invention to provide a PZT material of the foregoing type, which is useful for ferroelectric capacitors over a broad range of thicknesses, particularly in the range of from about 20 to about 150 nanometers.

A still further object of the invention is to provide a PZT material that is useful for ferroelectric capacitors over a broad range of pulse lengths, particularly in the range of from about 5 nanoseconds to about 200 microseconds.

Other objects and advantages of the invention will be more fully apparent from the ensuing disclosure and appended claims.

SUMMARY OF THE INVENTION

The present invention relates generally to a novel lead zirconium titanate (PZT) material, as well as to a deposition method for forming PZT thin films of such material, and ferroelectric capacitor structures employing such thin film material.

As used hereinafter, the following terms shall have the following definitions:

"Remanent polarization," $P_r$, is the polarization at zero volts after passing through $V_{op}$.

"Ferroelectric switched polarization," $P_{sw}=P^*-P^\wedge$, wherein $P^*$ is the polarization transferred out of the capacitor traversing from zero to $V_{op}$ volts when the capacitor starts at $P_r(-V_{op})$, and $P^\wedge$ is the polarization transferred out of the capacitor traversing from zero to $V_{op}$ volts when the capacitor starts at $P_r(V_{op})$. The pulse length is 0.23 milliseconds. The measuring instrument used to determine the values hereinafter set forth was a Radiant 6000 unit.

"Coercive E-field," $E_c$ is the electric field at which the polarization is zero during a polarization versus voltage hysteresis loop. The E-field frequency is 50 Hertz for this purpose.

"$E_{max}$" is the maximum E-field for the hysteresis loop measured with $E_{max}=3E_c$.

"Leakage current density," J, is measured at the operating voltage, $V_{op}$, and a step voltage response at 5 seconds.

"Retention" is the remanent polarization as measured by the method described in Integrated Ferroelectrics, Vol. 16 [669], No. 3, page 63 (1997).

"Cycling fatigue $P_{sw}$" is the ferroelectric polarization measured with a frequency of 0.5 MegaHertz or slower square pulse, at a 50% duty cycle, and a capacitor area of $\leq 10^{-4}$ $cm^2$.

"Dimensionally-scalable PZT" material means a PZT material that is un-doped and has useful ferroelectric properties for PZT thin film capacitors over a range of thickness of from about 20 to about 150 nanometers, and with lateral dimensions as low as 0.15 μm and lower, and corresponding capacitor areas from about $10^4$ to about $10^{-2}$ μm$^2$.

"E-field scalable PZT" material means a PZT material that is un-doped and has useful ferroelectric properties for PZT thin film capacitors over the range of film thickness of 20 to 150 nanometers, at a voltage below 3 Volts.

"Pulse length scalable PZT" material means a PZT material that is un-doped and has useful ferroelectric properties over a range of excitation (voltage) pulse length from 5 nanoseconds to 200 microseconds.

"Ferroelectric operating voltage" means a voltage that when applied to a PZT thin film in a capacitor causes the material to be dielectrically switched from one to another of its orientational polar states.

"Plateau effect determination" means establishing a correlative empirical matrix of plots of each of ferroelectric polarization, leakage current density and atomic percent lead in PZT films, as a function of each of temperature, pressure and liquid precursor solution A/B ratio, wherein A/B ratio is the ratio of Pb to (Zr+Ti), and identifying from the plots the "knee" or inflection point of each plot as defining a region of operation with respect to the independent process variables of temperature, pressure and liquid precursor solution A/B ratio, and conducting the MOCVD process at a corresponding value of the temperature, pressure and liquid precursor solution A/B ratio selected from such region of operation, as hereinafter described.

"Type 1 properties" means, collectively, a ferroelectric polarization $P_{SW}$ greater than 20 microCoulombs (μC) per square centimeter, a leakage current density (J) less than $10^{-5}$ amperes per square centimeter at operating voltage, a dielectric relaxation defined by $J^{-n}$ log (time) wherein n is greater than 0.5 and a cycling fatigue defined by $P_{sw}$ being less than 10% lower than its original value after $10^{10}$ polarization switching cycles.

"Type 2 properties" means, collectively, the following dimensionally scaled properties of ferroelectric polarization, coercive E-field, leakage current density, retention and cycling fatigue:

| Basic property | Thickness Scaling (t) | Lateral dimension scaling (l) |
| --- | --- | --- |
| Ferroelectric polarization ($P_{sw}$) | $P_{sw} > 40$ μC/cm$^2$ for t > 90 nm<br>$P_{sw} > 30$ μC/cm$^2$ for t > 50 nm<br>$P_{sw} > 20$ μC/cm$^2$ for t > 20 nm | $P_{sw} > 30$ for l > 1 μm<br>$P_{sw} > 20$ for l > 0.05 μm |
| Coercive E-field ($E_c$) | $E_c < 100$ kV/cm for t > 50 nm<br>$E_c < 150$ kV/cm for t > 20 nm | $E_c < 100$ kV/cm for l > 0.05 μm |
| Leakage current density (J) | $J < 10^{-5}$ A/cm$^2$ for t > 90 nm<br>$J < 10^{-4}$ A/cm$^2$ for t > 50 nm | $J < 10^{-4}$ A/cm$^2$ for l > 0.05 μm |
| Retention | <3%/natural log decade (t in hours) at 150° C., per procedure for t > 50 nm | <3%/natural log decade (t in hours) at 150° C., per procedure for l > 0.05 μm |
| Cycling fatigue $P_{sw}$ | <10% decrease after $10^{10}$ cycles for t > 50 nm | <10% decrease after $10^{10}$ cycles for l > 0.05 μm |
| | <10% decrease after $10^8$ cycles for t > 20 nm | |

"Un-doped" in reference to PZT film material means that the dopants and modifiers (heterologous atomic species that are added into the crystal structure of the PZT material and are responsible for the observed or enhanced ferroelectric properties of the material) are present in the material at concentrations of less than 1 atomic percent.

In one aspect, the present invention relates to a dimensionally scalable, pulse length scalable and/or E-field scalable ferroelectric PZT material.

Another aspect of the invention relates to a ferroelectric PZT material having Type 1 and/or Type 2 characteristics.

In another aspect, the invention relates to a ferroelectric PZT material that has at least one, more preferably at least two, still more preferably at least three, and most preferably all four, of the Type 1 properties.

In a further aspect, the present invention relates to a ferroelectric PZT material having at least one of the Type 2 properties and progressively more preferably having two, three, four or five of such properties.

The invention relates in another aspect to a ferroelectric PZT material capacitor comprising a ferroelectric PZT material of a dimensionally-scalable, pulse length scalable and/or E-field scalable character, and a capacitor area of from about $10^4$ to about $10^{-2}$ μm$^2$.

Another aspect of the invention relates to a FeRAM device, including a capacitor comprising a ferroelectric PZT material of a dimensionally-scalable, pulse length scalable and/or E-field scalable character, and a capacitor area of from about $10^4$ to about $10^{-2}$ μm$^2$.

In another aspect, the invention relates to a method of fabricating a ferroelectric PZT film on a substrate, comprising forming the film by liquid delivery MOCVD on the substrate under MOCVD conditions producing a ferroelectric film on the substrate having Type 1 and/or Type 2 characteristics.

A further aspect of the invention relates to a method of fabricating a ferroelectric PZT film on a substrate, comprising forming the film by liquid delivery MOCVD on the substrate under MOCVD conditions including nucleation conditions producing a dimensionally scalable, pulse length scalable and/or E-field scalable PZT film on the substrate.

Another aspect of the invention relates to a method of fabricating a ferroelectric PZT film on a substrate, comprising forming the film by liquid delivery MOCVD on the substrate under MOCVD conditions including temperature, pressure and liquid precursor solution A/B ratio determined by plateau effect determination from a correlative empirical matrix of plots of each of ferroelectric polarization, leakage current density and atomic percent lead in PZT films, as a function of each of temperature, pressure and liquid precursor solution A/B ratio, wherein A/B ratio is the ratio of Pb to (Zr+Ti).

A further aspect of the invention relates to a method of fabricating a ferroelectric PZT film on a substrate, comprising forming the film by liquid delivery MOCVD on the substrate under MOCVD conditions including Correlative Materials or Processing Requirements, to yield a ferroelectric PZT film having PZT Properties, wherein such Correlative Materials or Processing Requirements and PZT Properties comprise:

| PZT Properties | Correlative Materials or Processing Requirements |
| --- | --- |
| Basic properties: | |
| Ferroelectric polarization $P_{sw} > 20\ \mu C/cm^2$ | Film Pb concentration > threshold level; operation on A/B plateau above the knee region, and with temperature, pressure and gas phase A/B concentration ratio defined by plateau effect determination |
| Leakage current density $J < 10^{-5}$ A/cm$^2$ at operating voltage | Film Pb concentration within a range (between the minimum and maximum) on the A/B plateau, and with temperature, pressure and gas phase A/B concentration ratio defined by plateau effect determination |
| Dielectric relaxation For characteristic $J^{-n}$ log (time), n > 0.5 and J < 1% ferroelectric switching current from 0–100 ns. | Zr/Ti ratio < 45/55 Deposition P > 1.8 torr |
| Retention Maintenance of ferroelectric properties (ferroelectric domains) | Operation within ranges of temperature, pressure and gas phase A/B concentration ratio defined by plateau effect determination |
| Avoidance of cycling fatigue $P_{sw}$ < 10% decrease after $10^{10}$ cycles | Use of Ir-based electrodes |
| E-field scalability | Operation within ranges of temperature, pressure and gas phase A/B concentration ratio defined by plateau effect determination |
| Surface smoothness | Nucleation-growth conditions during film formation within ranges of temperature, pressure and gas phase A/B concentration ratio defined by plateau effect determination |
| Grain size | Nucleation-growth conditions during film formation within ranges of temperature, pressure and gas phase A/B concentration ratio defined by plateau effect determination |

A still further method aspect of the present invention relates to a method of fabricating a FeRAM device, comprising forming a capacitor on a substrate including a ferroelectric PZT material of a dimensionally-scalable, pulse length-scalable and/or E-field scalable character, wherein the PZT material is deposited by liquid delivery MOCVD under processing conditions yielding a ferroelectric film on the substrate having Type 1 and/or Type 2 characteristics as such ferroelectric PZT material.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
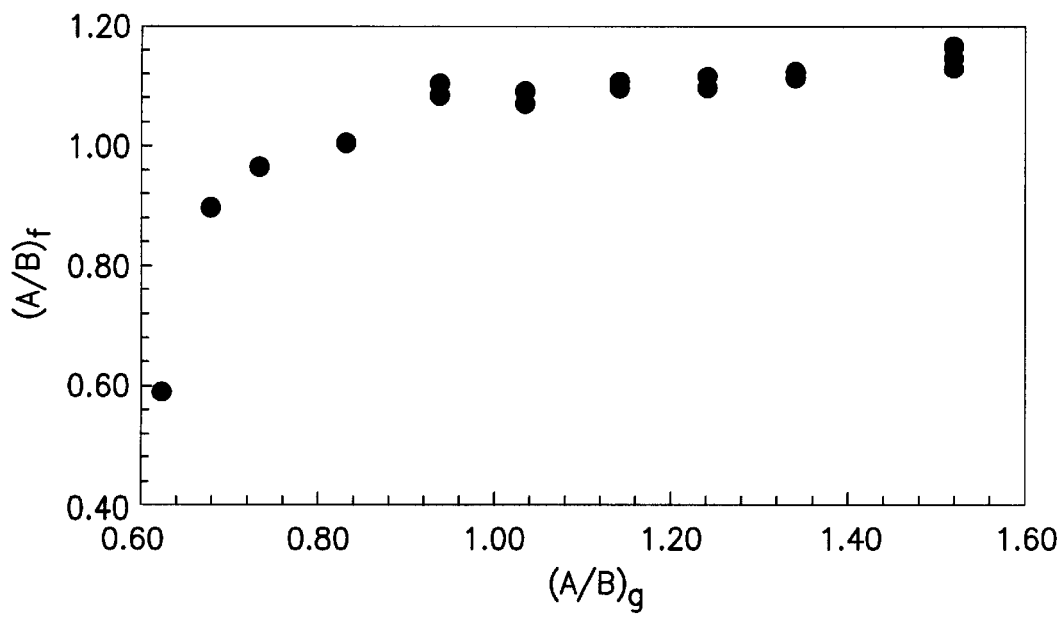
FIG. 1 is a graph of film composition $(A/B)_f$ as a function of gas-phase composition $(A/B)_g$ for a PZT thin film material, showing the insensitivity of the stoichiometry to the precursor concentration.

The present invention provides a unique PZT material that is scalable in character and provides major advantages over the prior art in application to the formation and use of PZT in ferroelectric thin film capacitor structures.

In contrast to the PZT materials previously used in the prior art, the PZT material of the present invention is useful for ferroelectric capacitors over a wide range of thicknesses, e.g., from about 20 nanometers to about 150 nanometers, and a range of lateral dimensions extending to as low as 0.15 $\mu$m. Corresponding capacitor areas (i.e., lateral scaling) in a preferred embodiment are in the range of from about $10^4$ to about $10^{-2}\ \mu$m$^2$.

The foregoing properties provide a dimensional scaling capability that is achievable without PZT film modification techniques such as acceptor doping or the use of film modifiers such as Nb, Ta, La, Sr, Ca and the like.

The novel PZT material of the present invention in one embodiment has Type 1 properties, viz., a ferroelectric polarization $P_{sw}$ greater than 20 $\mu$C/cm$^2$, a leakage current density J less than $10^{-5}$ A/cm$^2$ at $V_{op}$, a dielectric relaxation defined by $J^{-n}$ log(time) wherein n is greater than 0.5, and a cycling fatigue defined by $P_{sw}$ being less than 10% lower than its original value after $10^{10}$ polarization switching cycles.

Such PZT material is a substantial advance over the PZT materials of the prior art lacking such Type 1 properties, and the present invention provides a reproducible method of fabricating such material by liquid delivery metalorganic chemical vapor deposition.

The present invention relates in one aspect to a method to deposit thin film ferroelectric materials by MOCVD utilizing a liquid delivery technique. This technique affords precise compositional control by virtue of mixing liquid precursor solutions and flash vaporizing them. Flash vaporization has the added benefit of preventing unwanted premature decomposition of the precursor species. Further, tailored precursor chemistries may be employed that are compatible for forming the thin film material because the precursors do not undergo ligand exchange (or they have degenerate exchange) which prevents the formation of involatile species.

For thin film PZT and related materials, precise and repeatable compositional control is required in order to produce films of high quality. Physical deposition methods (e.g., sputtering, evaporation) of thin film deposition are deficient in this regard, as are traditional approaches to MOCVD involving the use of bubblers.

A process therefore is desired for the formation of thin films of PZT and related materials, which affords compositional control, provides uniformity of the thin film material over large areas, and achieves a high degree of conformality on the substrate structure as well as a high deposition rate. The deposited material should also be free of pinholes, since in capacitive structures and in many other devices, pinholes will result in an electrically shorted, useless device.

In accordance with the invention, the metalorganic precursors of the component metals of the desired $PbZr_xTi_{1-x}O_3$ film are introduced in liquid form, either as neat liquids or dilute solutions if the precursor is a liquid at ambient temperature and pressure (e.g., 25° C. and atmospheric pressure) conditions, or if the precursor composition is a solid at such ambient conditions, then as a solution of the precursor in a compatible solvent medium. The solvent medium may be of any suitable type that is compatible with the specific precursor composition employed, as is known and understood by those skilled in the art of liquid delivery MOCVD, and may be constituted by single-component solvent species, or alternatively by multicomponent solvent mixtures.

The metalorganic precursors utilized for such liquid delivery technique may for example comprise lead bis(2,2,6,6-tetramethyl-3,5-heptanedionate), $[Pb(thd)_2]$, as a Pb precursor; titanium bis(isopropoxide)bis(2,2,6,6-tetramethyl-3,5-heptanedionate), $[Ti(O-i-Pr)_2(thd)_2]$, as a Ti precursor; and zirconium tetrakis(2,2,6,6-tetramethyl-3,5-heptanedionate), $[Zr(thd)_4]$, as a Zr precursor. Alternatively, the lead precursor may comprise lead bis(2,2,6,6-tetramethyl-3,5-heptanedionate)N, N', N"-pentamethyl diethylenetriamine, $[Pb(thd)_2pmdeta]$, and the zirconium precursor may alternatively comprise zirconium bis(isopropoxide)bis(2,2,6,6-tetramethyl-3,5-heptanedionate), $[Zr(O-i-Pr)_2(thd)_2]$.

The solvent media used in the liquid delivery MOCVD process of the invention may suitably comprise by way of example the solvent compositions that are disclosed in U.S. patent application Ser. No. 08/414,504 filed Mar. 31, 1995 in the names of Robin A. Gardiner, et al., and issued on Dec. 8, 1998 as U.S. Pat. No. 5,846,275, U.S. patent application Ser. No. 08/484,654 filed Jun. 7, 1995 in the names of Robin A. Gardiner, et al., and U.S. patent application Ser. No. 08/975,372 filed Nov. 20, 1997 in the names of Thomas H. Baum, et al., which are compatible with the specific metalorganic precursors used for forming the $PbZrTiO_3$ thin film materials and efficacious in the constituent liquid delivery and chemical vapor deposition process steps. The disclosures of the foregoing patent applications and corresponding patents based thereon are hereby incorporated herein by reference in their entireties.

In one preferred embodiment the solvent media is comprised of a solution containing approximately 8 parts tetrahydrofuran (THF), 2 parts isopropanol and one part tetraglyme (parts by volume). In another embodiment, such as the case where $Pb(thd)_2$ is used, one or both of the isopropanol and tetraglyme would be excluded from the preferred solvent media. Other illustrative multicomponent solvent compositions include a solvent medium comprising octane: decane: polyamine in an 5:4:1 ratio, and a solvent medium comprising octane: polyamine in an 9:1 ratio. One particularly preferred single component solvent medium is tetrahydrofuran (THF).

The liquid precursor composition once formulated is introduced into a vaporization zone, in which the liquid is rapidly vaporized, e.g., by flash vaporization on a foraminous vaporization element (e.g., a porous frit element, or a wire, grid or other high surface area structural element) heated to suitable temperature, to produce a corresponding precursor vapor.

The precursor vapor then is transported to the chemical vapor deposition chamber, which may for example comprise a CVD reactor of known or conventional type. The CVD system may be suitably equipped to introduce the precursor vapor into the deposition chamber for contact with a heated substrate, at a temperature that is suitable to effect deposition of the metal constituents of the vapor onto the substrate element. For this purpose, the substrate may be mounted on a heated susceptor or other substrate mounting structure, with the spent vapor from the process being discharged from the deposition chamber and subjected to further treatment or processing in a known and conventional manner.

Further, the film as deposited may be further processed in any suitable manner, e.g., by annealing according to a specific time/temperature relationship, and/or in a specific atmosphere or environment, to produce the final desired thin film $PbZrTiO_3$ material.

In one embodiment of the present invention, the precursors for the metal components of the product film are dissolved in a solvent and flash vaporized at temperatures between about 100 to about 300° C. and transported into the MOCVD reactor with a carrier gas (e.g., Ar, $N_2$, $H_2$, He, or $NH_3$). The resulting carrier gas/precursor vapor mixture then may be mixed with an oxidizing co-reactant gas (e.g., $O_2$, $N_2O$, $O_3$ or mixtures thereof) and transported to the deposition chamber to undergo decomposition at a substrate heated to a temperature of from about 400° C. to about 1200° C. at chamber pressures in the range of from about 0.1 to about 760 torr. Other active oxidizing species may be used to reduce deposition temperature, as through the use of a remote plasma source.

Investigation in the field of PZT materials research has established the existence of regimes for CVD process parameters in which the film Pb composition is insensitive to changes in precursor concentrations (see, for example, M. De Keijser, P. Van Veldhoven and G. Dormans, *Mat. Res. Symp. Proc.*, Vol. 310 (1993) p.223–234; and J. Roeder, B. A. Vaartstra, P. C. Van Buskirk, H.R. Beratan, "Liquid delivery MOCVD of ferroelectric PZT," *Mat. Res. Symp. Proc.*, Vol. 415 (1996) p. 123–128).

This characteristic is highly desirable in application to the design and optimization of manufacturing processes, and the inventors have investigated film properties for films deposited over a range of precursor concentrations within this self-correcting regime. It has been discovered that although the PZT composition remains substantially independent of precursor concentration, the associated PZT film microstructure and properties can vary significantly. Furthermore, the inventors have discovered that proximity to the "edge" of the self-correcting regime is of primary importance rather than proximity to the stoichiometric composition. This is a significant finding relative to the prior art conventional wisdom that a few percent stoichiometric excess Pb is optimal.

The present inventors have demonstrated that MOCVD processes for deposition of PZT have the desirable property of the stoichiometry being largely insensitive to process conditions over a fairly wide range of process conditions. However, it has also surprisingly been found that the properties of deposited films with the same stoichiometric composition are not functionally equivalent. The present invention resolves this incongruity by an approach that identifies process conditions with optimum electrical properties.

In a primary aspect, the invention relates to a methodology for selection of CVD process conditions that result in PZT films with superior properties. The methodology exploits the "A/B plateau effect" to achieve the fabrication of capacitive PZT films whose electrical properties are congruent with optimum requirements of ferroelectric non-volatile (NV) memories such as ferroelectric random access memories (FeRAMs). The "A/B plateau effect" is described below, and is based on the concept that smoothness and grain size can be controlled by modifying specific nucleation and growth phenomena. The complete ensemble of deposition conditions and principles for selecting processing parameters, as described hereafter, result in PZT film properties that were previously considered by the art to be unachievable, especially low imprint for un-doped PZT, and E-field scaling to low thicknesses, e.g., to thicknesses as low as 20 nm.

The matrix of PZT properties and correlative materials or processing requirement(s) for achieving such properties is set out in Table A below.

TABLE A

| PZT property | Correlative Materials or Processing Requirement(s) |
| --- | --- |
| Basic properties: | |
| Ferroelectric polarization $P_{sw} > 20\ \mu C/cm^2$ | Film Pb concentration > threshold level; operation on A/B plateau above the knee region; the A/B plateau determines 3 process parameters: P, T and gas phase A/B concentration ratio |
| Leakage current density $J < 10^{-5}\ A/cm^2$ at operating voltage | Film Pb concentration within a range (between the minimum and maximum) on the A/B plateau; A/B plateau determines 3 process parameters: P, T and gas phase A/B concentration ratio |
| Dielectric relaxation For characteristic $J^{-n}$ log (time), n > 0.5 and J < 1% ferroelectric switching current from 0–100 ns. | Zr/Ti ratio < 45/55 Deposition P > 1.8 torr |
| Retention Maintenance of ferroelectric properties (ferroelectric domains) | Operation within ranges of P, T and gas phase A/B concentration ratio determined above |
| Avoidance of cycling fatigue $P_{sw} < 10\%$ decrease after $10^{10}$ cycles | Use of Ir-based electrodes |
| E-field scaling Achieving qualitative capacitor performance for films with reduced thickness, and at reduced voltages | Operation within ranges of P, T and gas phase A/B concentration ratio determined above |
| Surface smoothness | Nucleation-growth conditions during film formation within ranges of P, T and gas phase A/B concentration ratio determined above |
| Grain size | Nucleation-growth conditions during film formation within ranges of P, T and gas phase A/B concentration ratio determined above |

An illustrative specific process embodiment that may be used in connection with the Table A process parameters is set out below, as "Process Set A." As shown, Process Set A utilizes a specific precursor chemistry including precursor reagents and solvent compositions, substrate and barrier layer materials (the barrier layer being deposited or otherwise provided between the substrate and the PZT material layer), to provide an electrical environment suitable for the achievement of optimum electrical and performance properties of the PZT material, electrode materials of construction, carrier gas species and oxidant species.

Process Set A:

Process Condition/Material

Precursor Chemistry

Reagents: [Pb(thd)$_2$, Ti(O-i-Pr)$_2$(thd)$_2$; Zr(thd)$_4$]
Solvents: tetrahydrofuran, glyme solvents, alcohols, hydrocarbon and aryl solvents, amines, polyamines, and mixtures of two or more of the foregoing; examples of illustrative multicomponent solvent compositions are tetrahydrofuran:isopropanol:tetraglyme in a 8:2:1 volume ratio and/or octane:decane:polyamine in a volume ratio of 5:4:1.
Electrodes and Barriers Bottom Electrode: Ir bottom electrode on TiAlN barrier layer on substrate
deposition via sputtering using a collimator and deposition-etch processing
Top Electrode: Structures containing Ir and IrO$_x$ for top electrode
Carrier Gas, Oxidant: Ar, He, H$_2$ or other inert or non-adverse carrier gas;
O$_2$, O$_3$, N$_2$O, O$_2$/N$_2$O, etc. as oxidant medium
Deposition Conditions: Temperature, Pressure, Precursor Ratio: operate to exploit the plateau effect, in combination with appropriate gas delivery, oxidizer constituents, ratios, flow rates, liquid delivery, liquid flow rate, mixing and deposition time
Vaporizer: operate the vaporizer of the liquid delivery system to achieve the foregoing process conditions, as appropriate to the specific vaporizer apparatus employed; examples of vaporizer operating parameters that may
be involved include: back pressure, delivery tube ID, frit porosity, vaporizer temperature, gas co-injection, delivery tube/frit composition, and tube/frit installation procedure It will be appreciated that the Process Set A elements are by way of exemplification only, and that the specific precursor chemistries, carrier gas species, device structure layers, etc. may be widely varied in the broad practice of the present invention to achieve a scalable PZT film material within the scope of the present invention.

The thickness of the ferroelectric film material in the practice of the present invention may be widely varied. A preferred thickness for FeRAM applications is typically in the range of from about 20 to about 150 nanometers. Operating voltages for such PZT material films in FeRAM applications are typically below 3.3 Volts, down to much lower voltage levels.

The general formula for perovskite oxides is ABO$_3$, where specific metal elements occupy the A and B sites in the crystal lattice, and O is oxygen. For PZT, Pb is on the A site and Zr and Ti share the B site. Because the vapor pressure of PbO is lower when its incorporated in the perovskite structure, fairly wide ranges of CVD process parameters result in PZT films with the same or very slightly varying A/B site ratio ≈1.00. The existence of this A/B "self-correcting effect" is utilized to advantage in the present invention to achieve the formation of PZT material with the properties of: a ferroelectric polarization $P_{sw}$ greater than 20 $\mu C/cm^2$, a leakage current density J less than $10^{-5}$ A/cm$^2$ at $V_{op}$, a dielectric relaxation defined by $J^{-n}$ log(time) wherein n is greater than 0.5, and a cycling fatigue defined by $P_{sw}$ being less than 10% lower than its original value after $10^{10}$ polarization switching cycles (Type 1 properties).

Figure 2:
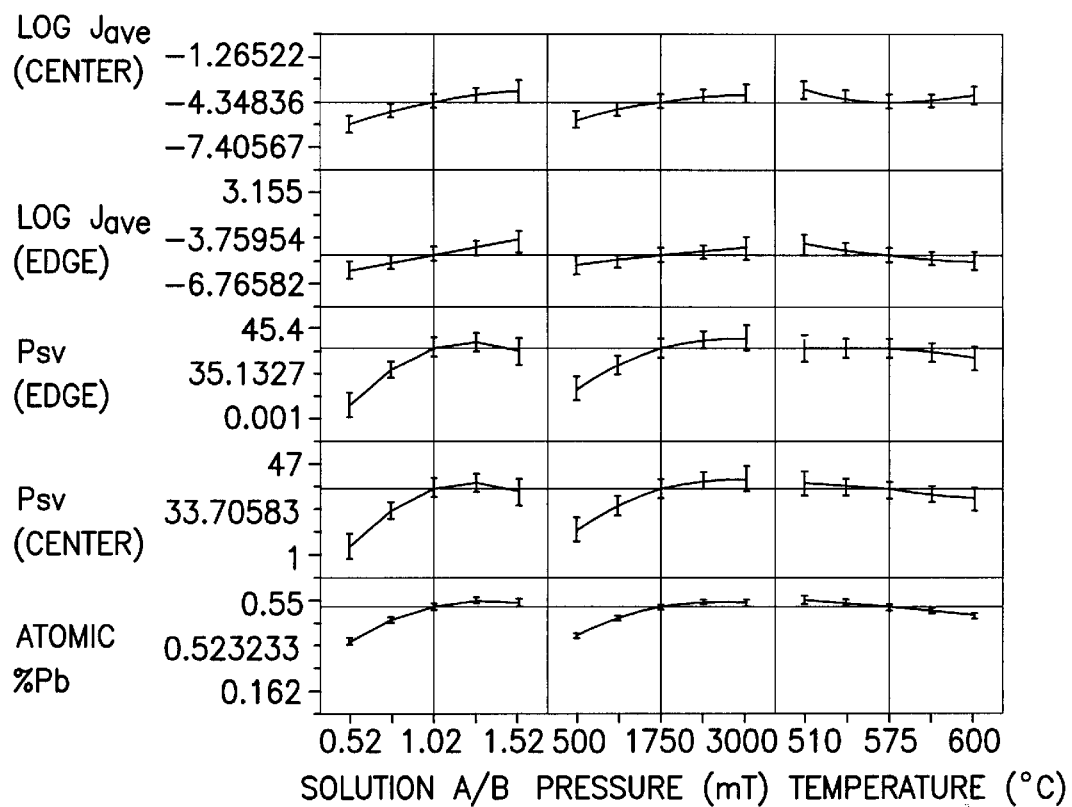
FIG. 2 is a model data matrix derived for empirically determined values of the logarithm of the leakage current density (Log J), the ferroelectric polarization ($P_{sw}$) and atomic % Pb in the film, as a function of pressure (P), temperature (T) and solution A/B ratio.

FIG. 2 is a model data matrix derived for empirically determined values of the logarithm of the leakage current density (Log J), the ferroelectric polarization ($P_{sw}$) and atomic % Pb in the film, as a function of pressure (P), temperature (T) and solution A/B ratio.

Model data from the matrix show the basic relationships between the independent (process variables) P, T and (A/B)$_{solution}$, on the dependent variables: atomic % Pb in the film, ferroelectric polarization ($P_{sw}$) and leakage current density (log J). Among these variables, (A/B)$_{solution}$ is equivalent to (A/B)$_{gas}$ since the precursor liquid reagent solution is vaporized to achieve a same gas-phase composition as is present in the liquid solution of the precursor.

Visual inspection of the various curves generated for the dependent variables (including average values for the central and edge regions of the ferroelectric films in the model data matrix of FIG. 2) shows a "knee" or inflection point beyond which the curve flattens in the direction of increasing value of the given independent process variables P, T and (A/B)$_{solution}$. By operating at or in the vicinity of the knee point, the superior PZT material of the invention is produced. The "vicinity" of the knee point will vary with the independent process variable; in the case of the solution A/B ratio and pressure, the vicinity is preferably within±25% of the knee point, and for the temperature, the vicinity is preferably within±5% of the knee point.

For the specific data shown in FIG. 2, this "knee" point is 1.02 for the solution A/B ratio, 1750 millitorr for the deposition pressure, and 575° C. for the deposition temperature. By selection of these independent variable values, the corresponding dependent values producing the superior PZT material of the invention produced with such A/B solution ratio, pressure and temperature may be readily determined, including a Log Javg center value of –35 amperes per square centimeter at operating voltage, Log $J_{avg}$ edge value of –6.77 amperes per square centimeter at operating voltage, a $P_{sw}$ edge value of 35.1 μC per square centimeter, a $P_{sw}$ center value of 33.7 μC per square centimeter, and an atomic % Pb of 52.3%.

The present invention thus encompasses a "plateau effect determination" comprising the steps of establishing a correlative empirical matrix of plots of each of ferroelectric polarization, leakage current density and atomic percent lead in PZT films, as a function of each of temperature, pressure and liquid precursor solution A/B ratio, wherein A/B ratio is the ratio of Pb to (Zr+Ti), and identifying from the plots the "knee" or inflection point of each plot as defining a region of operation with respect to the independent process variables of temperature, pressure and liquid precursor solution A/B ratio, and conducting the MOCVD process at a corresponding value of the temperature, pressure and liquid precursor solution A/B ratio selected from such region of operation, as hereinafter described.

Set out in Table B below is a tabulation listing of the most preferred material properties (Type 2 properties) of the thickness-scalable and dimensionally-scalable PZT material of the invention, wherein t is the film thickness of the PZT material, and l is the effective lateral dimension, defined as side of a square with an area that is the same as the capacitor area.

TABLE B

| Basic property | Thickness Scaling (t) | Lateral dimension scaling (l) |
|---|---|---|
| Ferroelectric polarization ($P_{sw}$) | $P_{sw} > 40$ μC/cm$^2$ for t > 90 nm $P_{sw} > 30$ μC/cm$^2$ for t > 50 nm $P_{sw} > 20$ μC/cm$^2$ for t > 20 nm | $P_{sw} > 30$ for l > 1 μm $P_{sw} > 20$ for l > 0.05 μm |
| Coercive E-field ($E_c$) | $E_c < 100$ kV/cm for t > 50 nm $E_c < 150$ kV/cm for t > 20 nm | $E_c < 100$ kV/cm for l > 0.05 μm |
| Leakage current density (J) | $J < 10^{-5}$ A/cm$^2$ for t > 90 nm $J < 10^{-4}$ A/cm$^2$ for t > 50 nm | $J < 10^{-4}$ A/cm$^2$ for l > 0.05 μm |
| Retention | <3%/natural log decade (time in hours) at 150° C., for t > 50 nm | <3%/natural log decade (time in hours) at 150° C., for l > 0.05 μm |
| Cycling fatigue $P_{sw}$ | <10% decrease after $10^{10}$ cycles for t > 50 nm <10% decrease after $10^8$ cycles for t > 20 nm | <10% decrease after $10^{10}$ cycles for l > 0.05 μm |

The invention contemplates the use of the "plateau effect" to achieve ferroelectric properties with the scaling properties specified in Table B, as well as the use of nucleation/smoothness methods to achieve ferroelectric properties with the scaling properties that are specified in Table B.

The ferroelectric PZT material of the invention thus is a dimensionally scalable material, and suitably comprises at least one of the Table A and/or Table B properties. The ferroelectric PZT material of the invention is also E-field scalable and pulse length scalable in character.

The PZT material of the present invention may be used to form capacitive structures such as FeRAM devices, as well as other microelectronic devices and precursor structures in which PZT may be used to advantage. The invention thus contemplates the provision of a microelectronic device structure including the PZT material of the invention, e.g., a pulse length scalable PZT material of the invention in combination with a power supply and associated power circuitry including such PZT material, as a microelectronic structure arranged for excitation of the PZT material, wherein the excitation is characterized by an excitation (voltage) pulse length in the range of from 5 nanoseconds to 200 nanoseconds.

By way of example, the PZT material may be used to fabricate a ferroelectric capacitor device structure, by forming a ferroelectric stack capacitor comprising a PZT ferroelectric material of the present invention as a capacitor element on a substrate containing buried transistor circuitry beneath an insulator layer having a via therein containing a conductive plug to the transistor circuitry. Such fabrication process may comprise the steps of patterning, deposition, etch, diffusion, ion implantation, ion bombardment, chemical modification, etc.

A more complete understanding of the present invention is enabled by the following detailed description, including specific reference to an illustrative device structure comprising a PZT material according to the invention.

Figure 3:
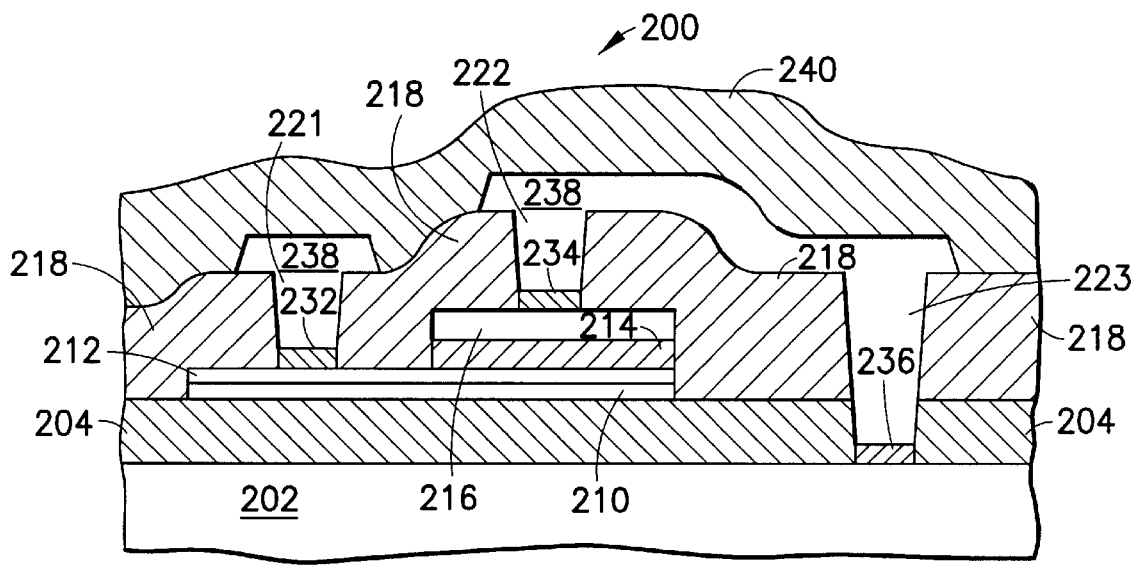
FIG. 3 is a schematic cross-section of a semiconductor device utilizing a stack capacitor configuration.

Referring now to FIG. 3, there is shown the cross-section of an integrated circuit semiconductor device 200, which is in the process of fabrication. Device 200 includes a semiconductor substrate 202 that may include active device structures, not shown, and an insulator layer 204. The semiconductor substrate 202 may be silicon, doped silicon, or another semiconductor material. The insulator layer 204 is deposited on the substrate 202 by any suitable deposition process. The insulator layer 204 may be, for example, silicon dioxide, silicon nitride, or some combination thereof.

A conductive diffusion barrier layer 210, such as titanium aluminum nitride TiAlN is deposited over the insulator layer 204. A layer of conductive material 212, such as iridium, iridium oxide, platinum or combinations thereof, is deposited over the conductive diffusion barrier layer 210. Next, a layer of high dielectric constant material 214, such as PZT, is deposited by MOCVD over the conductive layer 212. A second layer of conductive material 216, such as iridium, iridium oxide, platinum, or combinations thereof, is shown deposited over the layer of high dielectric constant material 214.

A diffusion barrier material such as titanium aluminum nitride (TiAlN) will substantially reduce the possibility of diffusion of oxygen during subsequent processing steps that require high temperatures in excess of 500° C. Other materials can be used for the diffusion barrier, such as those disclosed in U.S. patent application Ser. No. 08/994,089 filed Dec. 19, 1997 in the names of Peter S. Kirlin, et al., the disclosure of which hereby is incorporated herein by reference in its entirety.

FIG. 3 shows the portion of the device 200 after the device has been patterned with photoresist and etched. Desired portions of the conductive diffusion barrier layer, upper and lower layers of iridium or other conductive material and of the high dielectric constant material are left to form the upper electrode 216, capacitor dielectric 214, lower electrode 212, and lower electrode barrier layer 210.

A layer of interlevel dielectric 218 such as silicon dioxide or silicon nitride, is deposited over all. The layer of interlevel dielectric is patterned with photoresist and etch to form contact plug holes 221, 222, and 223. The insulator is etched down at the contract plug hole locations 221 and 222 until the iridium or other conductor of the lower electrode 212 and the upper electrode 216, respectively, are reached. Similarly the contact plug hole 223 is etched down through the insulator layers 218 and 204 until the semiconductor substrate is reached. Once the contact plug openings are prepared, the device 200 is ready for deposition of a layer of oxidation-barrier material.

FIG. 3 shows the semiconductor device 200 following an overall etch of the diffusion barrier layer leaving a diffusion barrier layer 232 in contact with the lower capacitor electrode 212, a diffusion barrier layer 234 in contact with the upper capacitor electrode 216, and a diffusion barrier layer 236 in contact with the semiconductor substrate 202. A transfer transistor of the memory cell may be located below the diffusion barrier layer 236, but it is not shown. As an alternative to the aforementioned diffusion barrier deposition scheme, the barrier layers 232, 234, and 236 could be deposited as a single continuous layer prior to the capacitor stack etch and deposition of insulating layer 218. According to this alternative configuration, the barrier layer could be patterned and used as a hardmask for the subsequent patterning of the capacitor stack. The alternate process flow would continue with the deposition and patterning of the insulating layer 218.

A conductive material, or metallization, is deposited over the interlevel dielectric 218 and the diffusion barrier layers 232, 234, and 236. The conductive material 238 makes contact with the diffusion barrier layers 232, 234, and 236. The conductive material 238 may be selected from a group of conductive materials such as aluminum, aluminum alloys, tungsten, tungsten alloys, iridium, and iridium alloys. The diffusion barrier layers 232, 234, and 236 significantly reduce the possibility of any diffusion of the layer of conductive material 238 to the capacitor electrodes 212 and 216 of the semiconductor substrate 202.

FIG. 3 shown the semiconductor device 200 after the layer of conductive material 238 is patterned and etched to form desired lead lines in the layer of conductive material. The pattern is formed of photoresist material. Etching is accomplished in accordance with well-established practices known to those of ordinary skill in the semiconductor manufacturing arts.

A layer of passivation dielectric 240 is deposited over the conductive material layer 238 and the interlevel dielectric 218. The passivation dielectric may be a material such as silicon dioxide, silicon nitride, or other insulator that can provide mechanical and electrical protection for the top surface of the semiconductor device. Material of the passivation dielectric layer 240 is deposited by well-known techniques.

The invention contemplates as an aspect thereof a microelectronic device structure comprising a PZT material of the present invention. While the invention has been describe herein with reference to specific features, aspects and embodiments, it will be appreciated that the utility of the invention is not thus limited, and that the invention contemplates variations, modifications and embodiments other than those shown and described herein. The aforementioned capacitor geometry may comprise a recessed capacitor geometry, for example, or other structures and conformations that will be readily apparent to those with ordinary skill in the art. Accordingly, the invention is to be broadly interpreted and construed to encompass all such variations and modifications The features and advantages of the invention are more fully shown with respect to the following illustrative examples.

EXAMPLE 1

The lead precursor chosen was lead bis(2,2,6,6-tetramethyl-3,5-heptanedionate) [Pb(thd)$_2$]. This compound has no appreciable vapor pressure at room temperature, which makes it much safer to handle than tetra-alkyl lead reagents. However, the low volatility of Pb(thd)$_2$ (0.05 Torr at 180° C.) requires the use of liquid precursor delivery. Titanium bis(isopropoxide)bis(2,2,6,6-tetramethyl-3,5-heptanedionate) [Ti(O-i-Pr)$_2$(thd)$_2$] was used as the titanium precursor. Zirconium tetrakis(2,2,6,6-tetramethyl-3,5-heptanedionate) [Zr(thd)$_4$] was used as the Zr source reagent. These compounds are extremely soluble in organic media and no possible detrimental ligand exchange occurs since the titanium atom is coordinatively saturated.

The following process conditions were applied:

| Operating Parameter | Process Condition |
| --- | --- |
| Substrate temperature | 550~610° C. |
| Bottom electrode | Ir/SiO$_2$/Si |
| Total reactor pressure | 1~10 Torr |
| Reactor wall temperature | ~210° C. |
| Carrier Ar flow | ~200 sccm |
| O$_2$ flow | 500 sccm |
| N$_2$O flow | 500 sccm |
| Total reagent solution concentration | 0.29 M |
| Reagent solution flow rate | 0.1~0.2 ml/min |

In a representative run, the film was deposited at 565° C. on Ir/SiO$_2$/Si. The pressure was 1.2 Torr, the oxidizer flow was a mixture of 500 sccm $O_2$ and 500 sccm $N_2O$, and the reagent flow rate was 0.14 ml/min for 32.5 minutes. XRF analysis gave the following thickness and composition data for the resulting $PbZrTiO_3$ film:

| Thickness ($\mu$m) | Pb (at. %) | Zr (at. %) | Ti (at. %) |
|---|---|---|---|
| 0.13 | 52.0 | 23.0 | 25.0 |

EXAMPLE 2

Solutions with a range of different Pb/(Zr+Ti) ratios were used over a series of deposition runs. This ratio is hereafter defined as $(A/B)_g$, denoting the conventional assignment of Pb to the "A" site, and Zr and Ti each to the "B" site in the perovskite cell, $ABO_3$. The subscript g denotes the gas-phase concentration in the reaction chamber, while $(A/B)_f$ denotes the equivalent ratio in the film.

The gas phase ratio of Zr/(Zr+Ti) was held constant at 0.612. Under the conditions given above in Example 1 and for the specific CVD reactor employed, the gas phase ratio of Zr/(Zr+Ti)=0.612 resulted in films with Zr/Ti~40/60, which for bulk materials yielded a tetragonal crystal structure and ferroelectric properties. This is a common composition chosen for FeRAM applications because of its high $P_r$ and the relative ease in forming the perovskite phase for lower Zr/Ti ratios.

Next, a series of PZT films was deposited with fixed deposition time, under the process conditions set out in Table 1 below; the effect on $(A/B)_f$ of $(A/B)_g$ determined in this empirical work is shown in FIG. 1. Nominal film thickness was 100 nm. For low $(A/B)_g$, $(A/B)_f$ increased monotonically with mole fraction of lead in the gas phase. Over the range $0.93<(A/B)_g<1.53$ a plateau was observed in $(A/B)_f$, in the range of 1.10 to 1.15. For these films the perovskite phase was the only crystalline phase present.

The appearance of this processing window, where film composition is insensitive to changes in the composition of Pb in the gas-phase, is rationalized in term of two competing processes: the formation of perovskite PZT via decomposition of Pb, Zr and Ti precursors, and the desorption of excess PbO from the growth surface. While we do not wish to be bound by any theory or mechanism in explanation for this processing window, it is hypothesized that the vapor pressure of PbO over PZT is significantly lower than it is for solid PbO, as is the case with bulk PZT (see the compiled bulk PZT material properties identified in K. H. Hartl and H. Rau, *Solid State Comm.*, 7, 41 (1969)).

TABLE 1

| CVD deposition conditions | |
|---|---|
| Precursors | $Pb(thd)_2$, $Zr(thd)_4$, $Ti(O$-$i$-$Pr)_2(thd)_2$ |
| Solution molarity | 0.29 M |
| Liquid flow rate | 0.14 ml/min |
| Substrate temperature | 550° C. |
| Pressure | 1.2 torr |
| Deposition rate | 3.5 nm/min |
| Substrate | $Ir/MgO/SiO_2/Si$ |

Under process conditions in which the kinetics of PZT formation are fast, and PbO volatility is high, single-phase, stoichiometric PZT can be formed.

The presence of the plateau at $(A/B)_f$ values exceeding 1.00 may be influenced by inaccuracy in the XRF measurement or by excess Pb diffused into the bottom electrode. Analysis of incorporation efficiencies for the metallic constituents revealed a decrease in Pb efficiency for $(A/B)_g>0.83$, while Zr and Ti efficiencies remained nearly constant over the same range. This is consistent with the appearance of the plateau, and the absence of PbO from XRD analysis of the films. Film thickness decreased slightly with increased $(A/B)_g$. This corresponded to an approximate growth rate decrease from 3.8 to 3.2 nm/min.

The as-deposited films were all smooth, dense, and fine-grained. The roughness and grain size values calculated from these images are given in Table 2 below. The measured film roughness was insensitive to gas phase composition and was approximately double the starting surface roughness of the Ir films used as substrates.

With increasing $(A/B)_g$, the grain size increased as did the extent of faceting, suggesting an enhanced surface mobility. This is believed to be a consequence of the higher PbO surface coverage that must be present during growth at higher gas-phase Pb concentrations if the previously described growth model is valid. The faceting in the high-Pb sample revealed predominately square features indicative of the presence of PZT (001)-type orientations, a conclusion also supported by the x-ray diffraction results.

TABLE 2

Summary of AFM data for PZT/Ir/MgO layers.
Film thickness is nominally 100 nm.

| $(A/B)_g$ | $(A/B)_f$ | RMS roughness (nm) | Grain size (nm) |
|---|---|---|---|
| 0.631 | 0.59 | 6.6 | 67 |
| 0.731 | 0.97 | 8.4 | 72 |
| 0.831 | 1.01 | 7.8 | 86 |
| 1.031 | 1.08 | 7.7 | 91 |

X-ray diffraction analysis revealed single perovskite phase for films deposited with $(A/B)_g \geq 0.83$. For $(A/B)_g<0.83$, an additional peak was observed at $2\Theta=29.9°$. The intensity of this peak decreased with increasing $(A/B)_g$ and was attributed to formation of the undesirable pyrochlore phase under lead-deficient deposition conditions.

PZT films on Ir/MgO displayed dominant (001) and (101) PZT orientations; furthermore, the (001)/(101) ratio of PZT peak intensities increased with increased $(A/B)_g$, i.e., oriented toward the tetragonal c-axis with a c-axis lattice constant of 0.406 nm. No appreciable (111) PZT texture was observed on Ir/MgO. X-ray diffraction of the as-received substrates revealed principally (111) oriented Ir; however, a considerable (200) Ir peak was present.

The best electrical properties were found for films with $(A/B)_g$ just above the knee in the curve shown in FIG. 1. Films with much higher or much lower $(A/B)_g$ were electrically shorted. For 3V operation, the remanent polarization ($2P_r$) and coercive voltage ($V_c$) were measured to be 85 $\mu C/cm^2$ and 0.77 V, respectively, for a 150 nm thick film deposited at $(A/B)_g=0.93$. This high value of remanent polarization is attributable to the strong preferred (001) orientation and the high degree of crystallization obtained on the Ir substrate.

EXAMPLE 3

A central-composite-design experiment was used to probe a large volume of process space and assess interactions between principal process variables. Deposition temperature (550, 575, 600° C.) and pressures (500, 1750, 3000 mTorr) were independently varied at five different values of $(A/B)_g$:

(0.53, 0.73, 0.93, 1.13, 1.53). A constant deposition time of 1660 seconds was used.

Compositionally, a plateau onset in $(A/B)_f$ was observed at $(A/B)_g$=0.93. For a given pressure, film lead content was observed to decrease with increased deposition temperature. Furthermore, incorporation efficiencies of both lead and titanium decreased with increasing $(A/B)_g$ for all temperatures.

Electrically, the best samples arose from the conditions at the center of the design (575° C., 1.75 Torr, $(A/B)_g$~1). Most of the good samples displayed a (−) voltage offset. There was no appreciable center-to-edge (wafer) effect. Leakage seemed to behave better for lower Pb and for thicker samples (~130 nm up to ~2.5 V).

EXAMPLE 4

Alternative zirconium oxide precursors are required, which are more volatile than $Zr(thd)_4$ and which also have lower thermal stability to be more compatible with the surface decomposition of $Pb(thd)_2$, for example.

Figure 4:
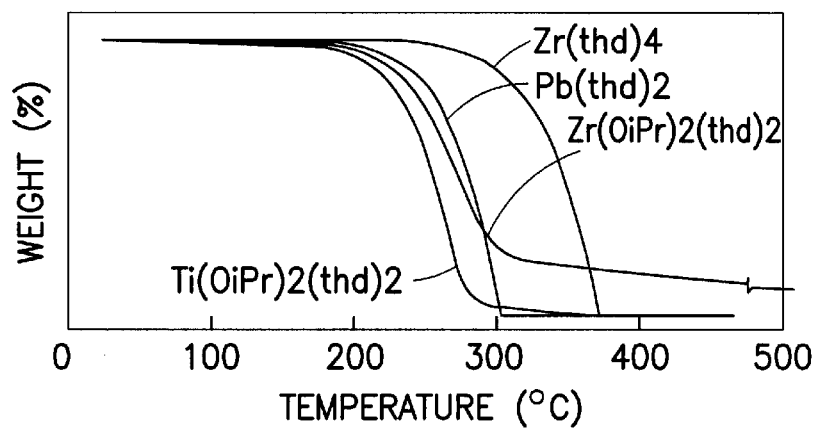
FIG. 4 is a plot of TGA data comparing Pb and Ti compounds with Zr(thd)$_4$ and Zr(O-i-Pr)$_2$(thd)$_2$.

FIG. 4 shows comparative TGA data for $Pb(thd)_2$, $Ti(O-i-Pr)_2(thd)_2$ and two selected Zr compounds: $Zr(thd)_4$ and $Zr(O-i-Pr)_2(thd)_2$. Although the $Zr(O-i-Pr)_2(thd)_2$ compound possesses an undesirable residuals content of nearly 20% at 400° C., it possesses a desirable thermal stability match with the Pb and Ti compounds commonly used for MOCVD PZT.

MOCVD PZT depositions were conducted on standard Ir/TiAlN bottom electrodes (BEs) using the novel $Zr(O-i-Pr)_2(thd)_2$ (Zr-2-2) compound with a vaporizer temperature set to 200° C. Additional depositions were processed using the standard $Zr(thd)_4$ (Zr-0-4) compound at a vaporizer temperature of 203° C. All other deposition conditions were held constant. Following PZT deposition, Pt top electrodes (TEs) were e-beam evaporated, and the samples were annealed at 650° C. in flowing argon for 30 min.

Composition and electrical data for the Zr-2-2 samples are presented along with data collected from the Zr-0-2 samples. The Zr-2-2 samples, though appreciably lower in Pb and Zr content than the Zr-0-4 samples, were electrically comparable.

In addition to the $Zr(O-i-Pr)_2(thd)_2$ precursor, MOCVD PZT may be prepared using still other novel Zr source precursors. For example, $Zr_2(O-i-Pr)_6(thd)_2$ has good ambient stability, high volatility and excellent thermal compatibility with Pb and Ti precursors.

TABLE 3

Composition and electrical data for MOCVD PZT films deposited using $Zr(O-i-Pr)_2(thd)_2$ and $Zr(thd)_4$

|  | $Zr(O-i-Pr)_2(thd)_2$ | $Zr(thd)_4$ |
| --- | --- | --- |
| % Pb (at. %) | 49.5 ± 0.07 | 51.8 ± 0.12 |
| Zr:(Zr + Ti) | 0.322 ± 0.001 | 0.443 ± 0.008 |
| efficiency Pb | 5.99 ± 0.049 | 7.43 ± 0.15 |
| efficiency Zr | 6.54 ± 0.078 | 4.36 ± 0.16 |
| efficiency Ti | 9.31 ± 0.035 | 10.7 ± 0.13 |
| t(nm) | 125 | 128 |
| $P_{SW}(\mu C/cm^2)(2V)$ | 36 | 38 |
| $\pm J(A/cm^2)(2V)$ | $7.4 \times 10^{-6}$; $-1.5 \times 10^{-6}$ | $<3 \times 10^{-6}$ for both polarities |

EXAMPLE 5

A number of samples are made up using PZT material formed in accordance with the present invention. The samples are comprised of bottom electrodes formed by sputtering techniques, deposition on the electrodes of PZT material in accordance with the present invention, followed by deposition of top electrodes through a shadow mask by e-beam deposition. The PZT deposition time was varied between 165 sec and 4065 sec to target film a thickness between 10 nm and 260 nm.

Electrical testing of the samples provides electrical characteristics of the capacitor structures that validate the thickness, pulse length and area scaling properties, including ferroelectric polarization, cycling fatigue, etc., of the ferroelectric PZT material of the present invention.

Figure 5:
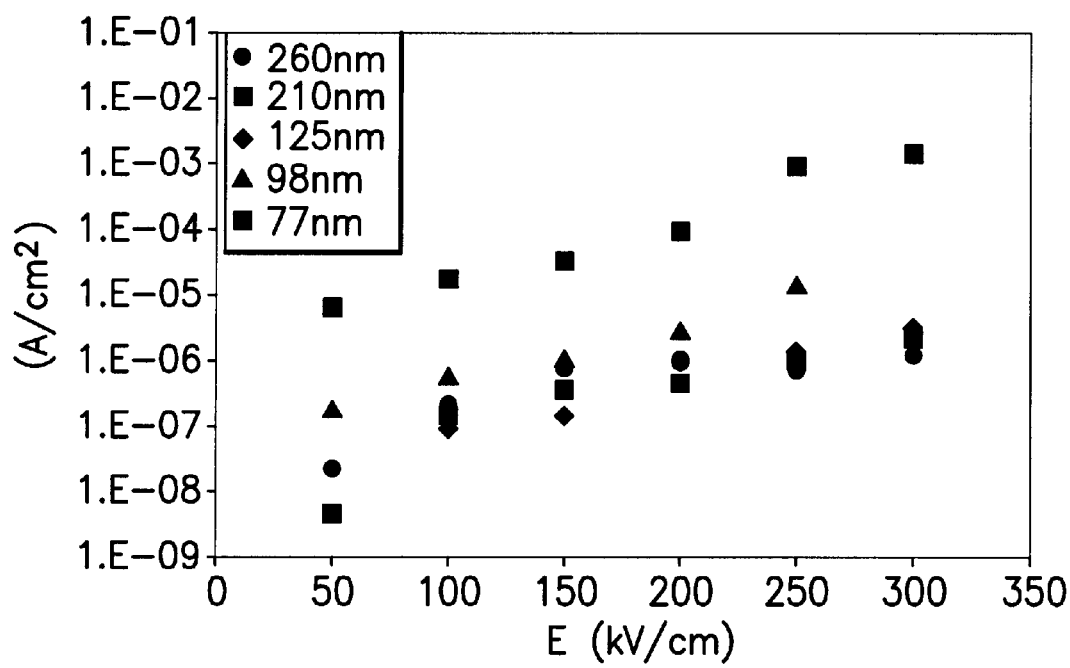
FIG. 5 is a plot of current density versus E-field for PZT films varying thickness showing the current density is only weakly dependent on film thickness above ~125 nm.

Leakage current density versus E-field is given in FIG. 5. The high "leakage" for the 77 nm film was directly confirmed. The qualitatively different electrical behavior for films below a thickness threshold may be due to the high relative roughness (roughness/thickness), which results in some extremely thin regions in thinner films. Locally high E-fields are expected in those cases. Current density for the thicker films in the set (>77 nm) showed remarkably consistent E-field dependence. Leakage in both polarities was in the $10^{-6}$ to $10^{-7}$ A/cm$^2$ range for 150 kV/cm. (150 kV/cm corresponds to 1.9 V for the 125 nm film, for example.)

Leakage was one of four properties that was insensitive to thickness when plotted as a function of E-field; the other properties were coercive voltage ($V_c$), polarization saturation ($P_{sw}$ versus $V_{op}$), and fatigue endurance.

Figure 6:
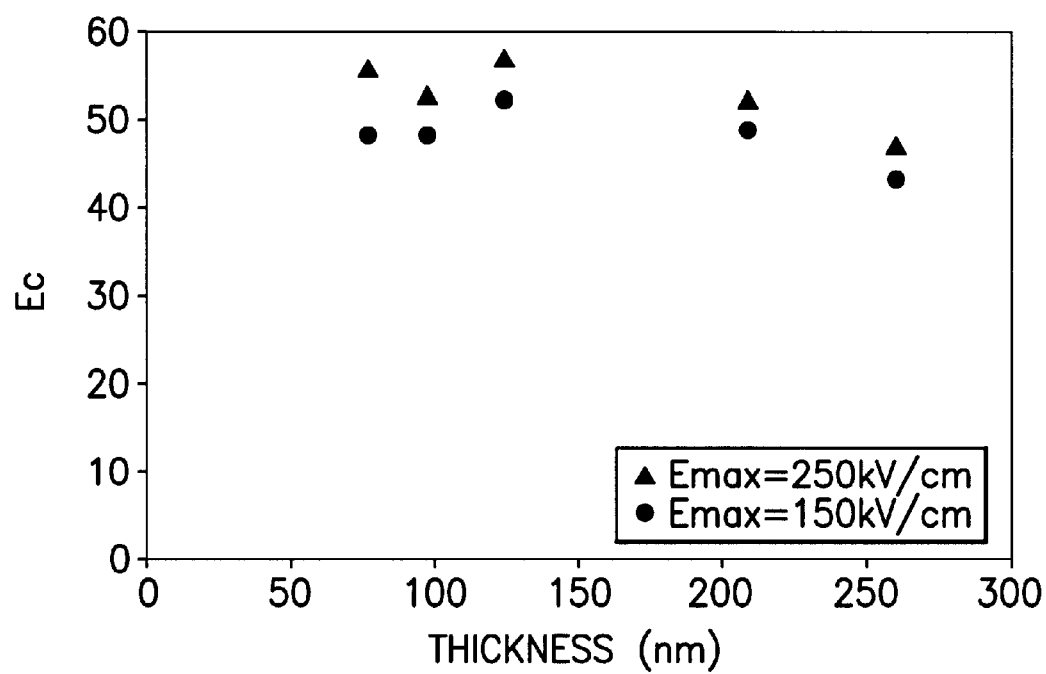
FIG. 6 is a plot of coercive field ($E_c$) versus film thickness showing that $E_c$ is nearly independent of film thickness.

The coercive voltage for each sample was determined from the relation $3V_c(measured)=V_{op}$ and the calculated values of $E_c$ based on that method are given in FIG. 6. For PZT films greater than 77 nm thick, $E_c$ was approximately 50 kV/cm.

Figure 7A:
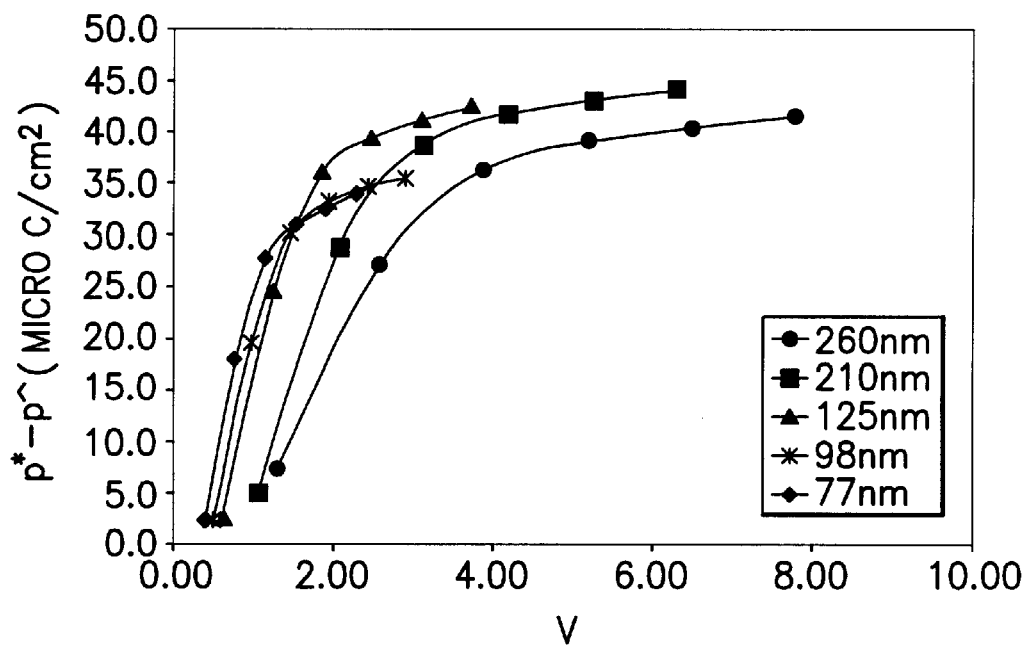
FIG. 7 is a plot of a) $P_{sw}$ versus voltage; and b) $P_{sw}$ versus electric field.
Figure 7B:
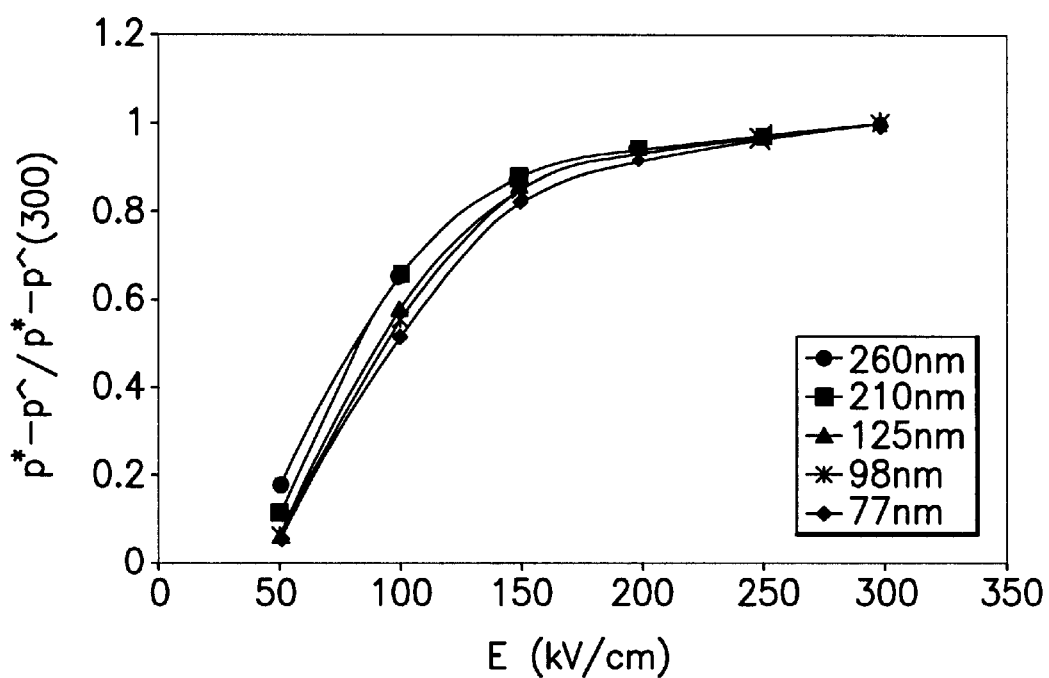

Pulse measurements were used to investigate polarization saturation. FIG. 7 shows the dependence of switched polarization on voltage and E-field. The data shows the expected increase of polarization for higher voltages. Clear saturation behavior is seen for the thicker films, which can withstand higher fields. For 125 nm and thicker films, saturated Psw>40 $\mu C/cm^2$. Normalized to $P_{sw}$ near saturation (300 kV/cm), $P_{sw}$ versus E is nearly independent of film thickness. For all of the samples $P_{sw}$ reaches nearly 90% of it maximum value at $3E_c$ (~150 kV/cm).

Figure 8:
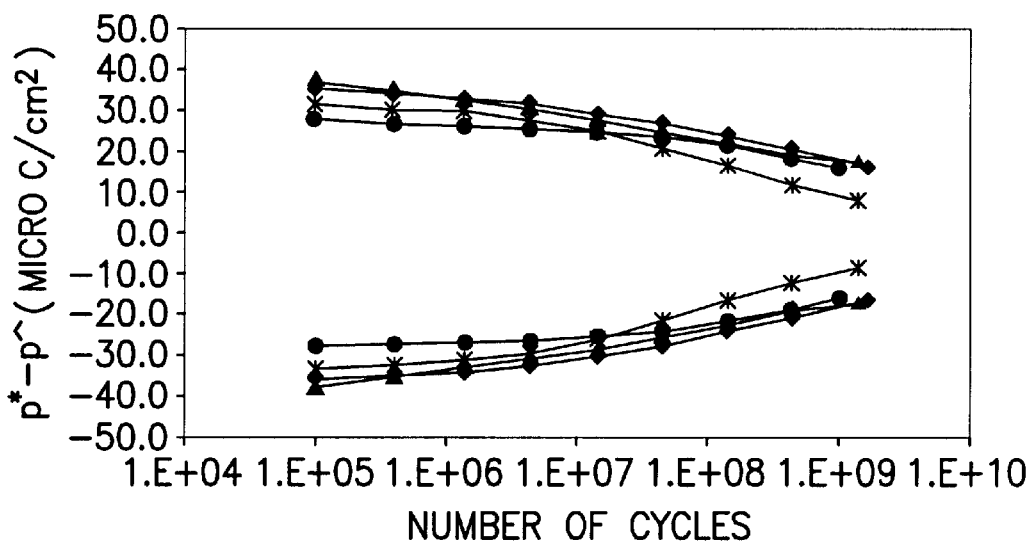
FIG. 8 is a plot of P*–P^ versus number of cycles for PZT films showing that fatigue is nearly independent of film thickness.

Fatigue properties for this sample set also displayed consistent properties in terms of E-field scaling (FIG. 8). Fatigue measurements were made at 150 kV/cm, which corresponds to $3E_c$. The fatigue waveform was a square wave with a period of $10^{-5}$ seconds. Fatigue is nearly independent of PZT thickness with a reduction in $P_{sw}$ by ~50% at $10^9$ cycles.

Static imprint is manifested as an asymmetry in coercive voltage, and is defined as $[V_c(-)+V_c(+)]/2$. Imprint voltage was probed via repeated measuring, poling, and annealing of a single capacitor. Following an initial measurement of $V_c$ (+and −) at time=0; capacitors were poled positive or negative to 2.5 V and then annealed at 150° C. (air) for 20 min. After cooling, the same (poled) capacitors were re-measured. Additional measurements were repeated following anneals of 24 min. (i.e. 45 min. elapsed time) and 45 min. (90 min. elapsed time).

Figure 9:
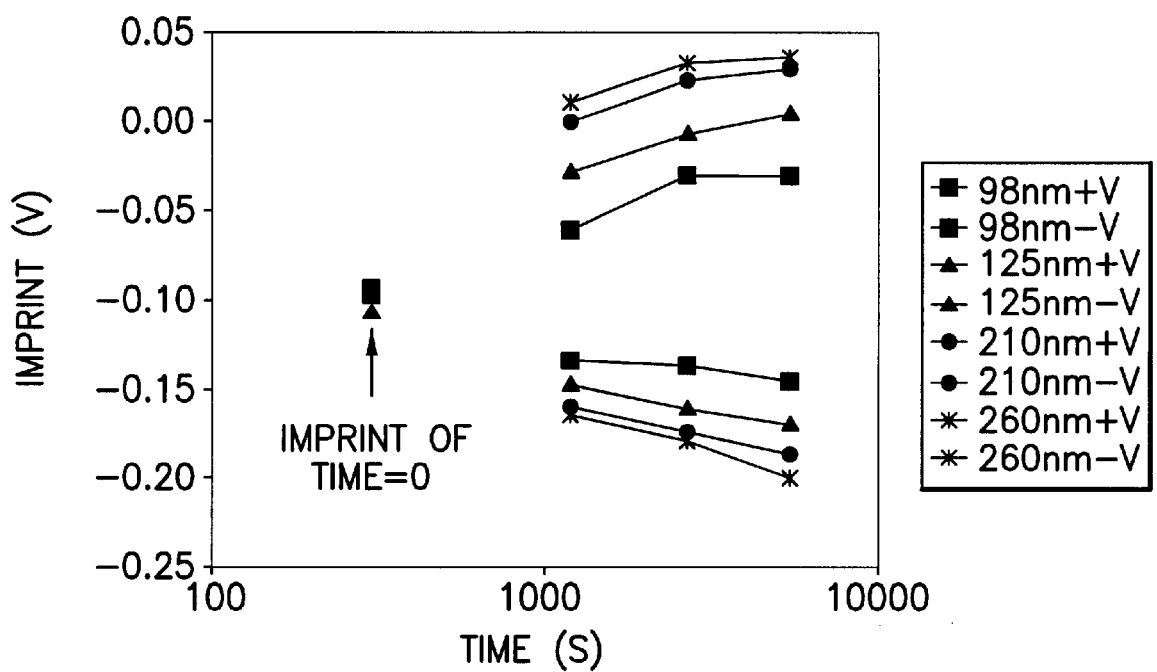
FIG. 9 is a plot of imprint behavior for PZT films of varying thickness.

FIG. 9 show a semi-log plot of imprint voltage versus time. The samples had nearly identical imprint at time=0 (~0.1 V). It is evident the imprint increases significantly at some time prior to the first measurement at 20 minutes. Thinner films were observed to have a lower imprint rate than thicker films. This trend suggests analyzing the data in terms of an imprint E-field.

EXAMPLE 6

In order to simplify test equipment and sample preparation during the development of ferroelectric materials, electrical testing has traditionally been conducted with pulse widths on the order of 1mS and capacitor areas on the order of $10^4$ $\mu m^2$. A disadvantage of this testing regimen is its inability to demonstrate the viability of electrical properties at scales appropriate for devices (i.e. 25nS pulses and $10^2$ $\mu m^2$). The market trend is toward devices that operate on increasingly shorter time scales and with smaller capacitor areas, hence scaling issues will be critical to future device success.

The sample used for these measurements originated with a 6-inch diameter Si wafer with an Ir bottom electrode, standard PZT, and a top electrode that consisted of 40 nm of $IrO_2$ and 60 nm of Ir, as described in Process Set A. Individual capacitors were defined using patterned photoresist and reactive ion etching in a $Cl_2/Ar/O_2$ mixture. Following patterning the sample was annealed at 650° C. in flowing oxygen for 30 min.

Figure 10:
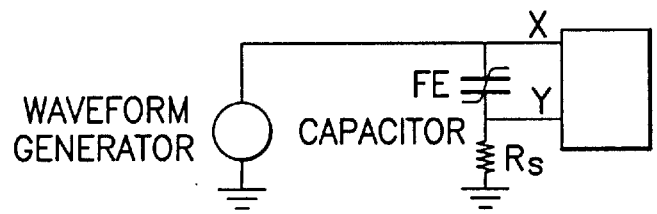
FIG. 10 shows the test configuration for the shunt method of ferroelectric pulse testing.
Figure 11:
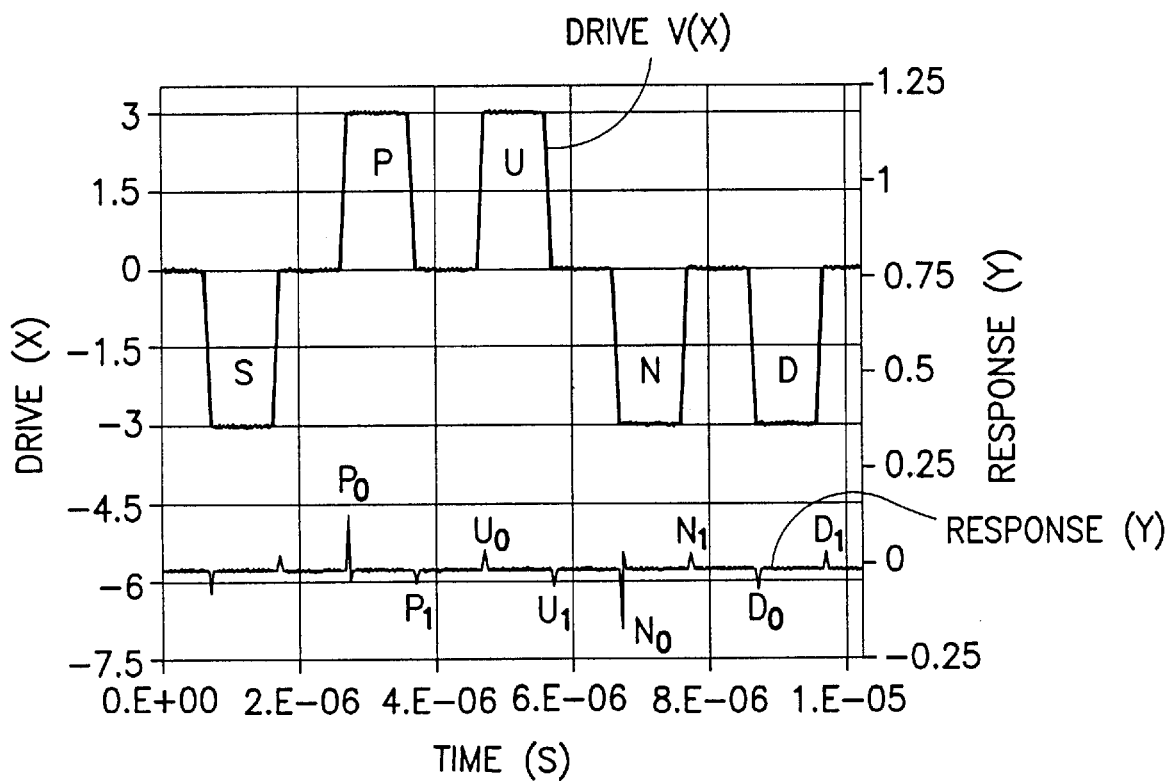
FIG. 11 is a plot of test signal and response signal versus time for a 10 $\mu$m×10 $\mu$m capacitor tested with a 1 $\mu$s pulse.

The test system consisted of an SRS DS345 arbitrary waveform generator, a Tektronix 620B digital storage oscilloscope, and a shunt resistor as shown in FIG. 10. Details of this testing protocol are further described in P. K. Larsen, G. Kampschoer, M. Ulenaers, G. Spierings and R. Cuppens, Applied Physics Letters, Vol. 59, Issue 5, pp. 611–613 (1991). A standard square-pulse ferroelectric pulse train was used. This pulse train consisted of one negative polarity pulse, followed by two positive pulses and two negative pulses (set, positive, up, negative, down). A typical drive signal, as measured at position X in FIG. 10, and response signal as measured at position Y in FIG. 10, are shown in FIG. 11.

The total charge passing from the ferroelectric capacitor to ground within each response pulse can be calculated from:

Charge: $Q = (1/R_S) \int V\, dV$

Ferroelectric switching occurs when a ferroelectric capacitor that has been previously poled by a negative (positive) pulse is poled up (down) by a subsequent positive (negative) pulse. $Q_{sw}$ is defined to be the difference in total charge contained within a switching pulse and a non-switching pulse:

$Q_{sw} = (S_0 + S_1) - (P_0 + P_1)$ where $S_0$ and $S_1$ are the leading and trailing edge response pulses for the first switching pulse and $P_0$ and $P_1$ are the leading and trailing edge pulses for the first non-switching pulse (FIG. 11).

Figure 12:
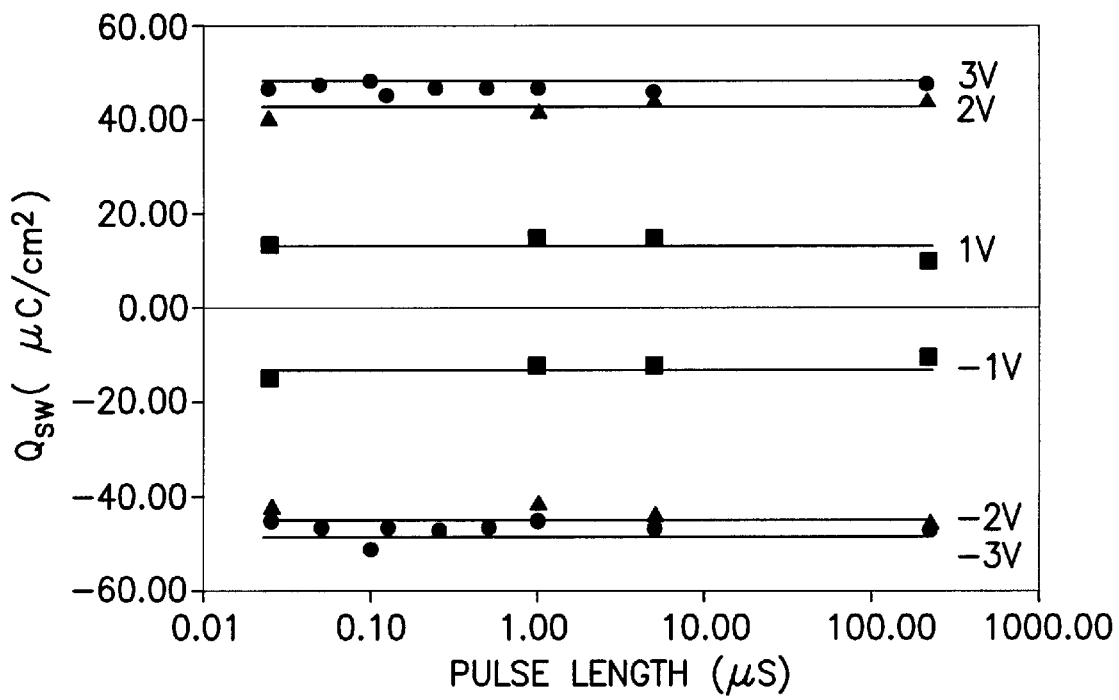
FIG. 12 is a plot of $Q_{sw}$ versus pulse length for various applied voltages showing $Q_{sw}$ to be independent of pulse length over the range investigated.

Measurements were made as described above with 1, 2 and 3 V pulses and pulse lengths between 25 nS and 0.22 mS. The polarization was found to be independent of pulse length over the range investigated (FIG. 12).

Figure 13:
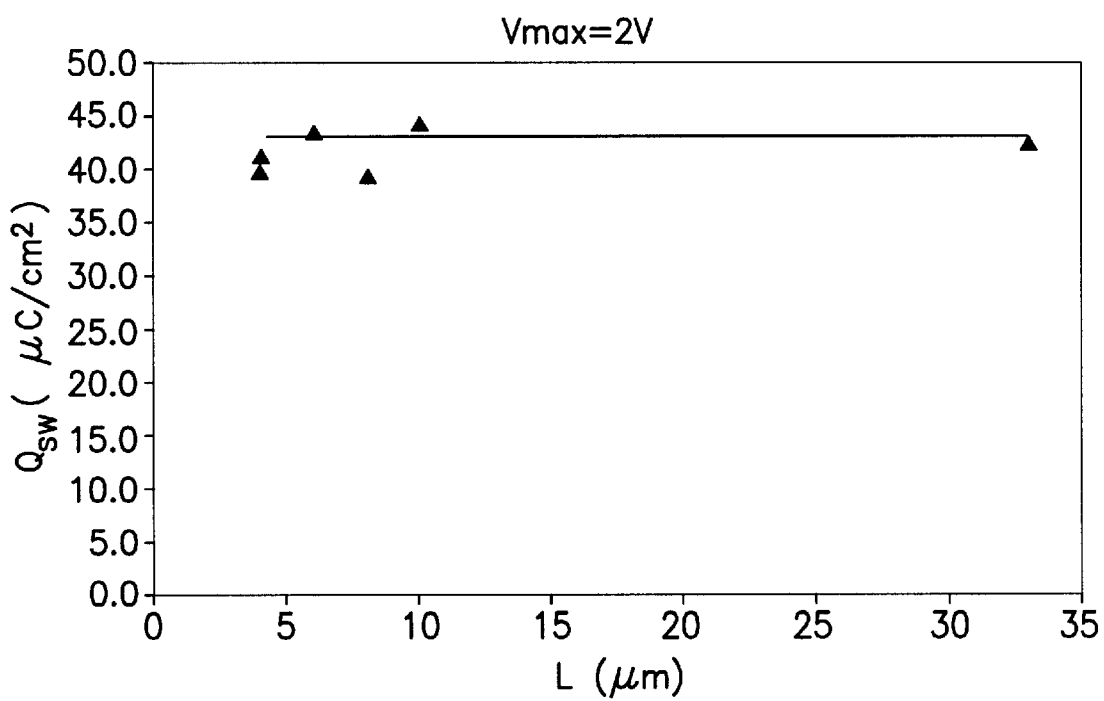
FIG. 13 is a plot of $Q_{sw}$ versus capacitor dimension showing $Q_{sw}$ to be independent of area over the range investigated.

Additionally, area scaling was investigated using 1 $\mu S$ pulses and square capacitors from 33 $\mu m \times 33$ $\mu m$ down to 4 $\mu m \times 4$ $\mu m$. $Q_{sw}$ was also found to be independent of capacitor dimension over the range investigated (FIG. 13).

While the invention has been illustratively described herein with reference to specific aspects, features and embodiments, it will be appreciated that the utility and scope of the invention is not thus limited and that the invention may readily embrace other and differing variations, modifications and other embodiments. The invention therefore is intended to be broadly interpreted and construed, as comprehending all such variations, modifications and alternative embodiments, within the spirit and scope of the ensuing claims.

What is claimed is:

1. A ferroelectric PZT material, having a dimensionally scalable, pulse length scalable and/or E-field scalable character.

2. A ferroelectric PZT material having a dimensionally scalable character.

3. A ferroelectric PZT material having a pulse length scalable character.

4. A ferroelectric PZT material having an E-field scalable character.

5. A ferroelectric PZT material having a dimensionally scalable character and a pulse length scalable character.

6. A ferroelectric PZT material having a dimensionally scalable character and an E-field scalable character.

7. A ferroelectric PZT material having a pulse length scalable character and an E-field scalable character.

8. A ferroelectric PZT material, having a dimensionally scalable, pulse length scalable and E-field scalable character.

9. The PZT material of claim 1, having a thickness of from about 20 to about 150 nanometers.

10. A ferroelectric PZT material, having a dimensionally scalable, pulse length scalable and/or E-field scalable character and a ferroelectric operating voltage below 2 Volts.

11. The PZT material of claim 1, having at least one of Type 1 properties.

12. The PZT material of claim 11, wherein at least one of said Type 1 properties includes a ferroelectric polarization $P_{sw}$ greater than 20 $\mu C$ per square centimeter.

13. The PZT material of claim 11, wherein at least one of said Type 1 properties includes a leakage current density J less than $10^{-5}$ amperes per square centimeter at a ferroelectric operating voltage of the material.

14. A ferroelectric PZT material, having at least one of Type 1 properties, which includes a dielectric relaxation defined by $J^{-n}$ log (time) wherein n is greater than 0.5.

15. The PZT material of claim 11, wherein at least one of said Type 1 properties includes a cycling fatigue defined by $P_{sw}$ being less than 10% lower than its original value after $10^{10}$ polarization switching cycles.

16. The PZT material of claim 11, having at least two of Type 1 properties.

17. A ferroelectric PZT material, having at least three of Type 1 properties.

18. A ferroelectric PZT material, having all of said Type 1 properties.

19. The PZT material of claim 1, having at least one of Type 2 properties.

20. The PZT material of claim 19, wherein at least one of said Type 2 properties includes ferroelectric polarization, $P_{sw}$.

21. The PZT material of claim 19, wherein at least one of said Type 2 properties includes coercive E-field, $E_c$.

22. The PZT material of claim 19, wherein at least one of said Type 2 properties includes leakage current density, J.

23. A ferroelectric PZT material, having at least one of Type 2 properties, which includes retention.

24. A ferroelectric PZT material, having at least one of Type 2 properties, which includes cycling fatigue of ferroelectric polarization.

25. The PZT material of claim 19, having at least two of Type 2 properties.

26. The PZT material of claim 19, having at least three of Type 2 properties.

27. A ferroelectric PZT material, having at least four of Type 2 properties.

28. A ferroelectric PZT material, having all of said Type 2 properties.

29. A ferroelectric PZT material, having (1) a dimensionally scalable, pulse length scalable and/or E-field scalable character; (2) at least one of Type 1 properties; and (3) at least one of Type 2 properties.

30. A capacitor comprising a ferroelectric PZT material according to any one of claims 1 to 29.

31. The capacitor of claim 30, having a capacitor area of from about $10^4$ to about $10^{-2}$ $\mu m^2$.

32. The capacitor of claim 30, wherein the PZT material is between a bottom electrode formed of a material comprising iridium and/or platinum, and a top electrode formed of a material comprising iridium and/or iridium oxide.

33. The capacitor of claim 30, constituting a stack capacitor.

34. A microelectronic device structure, comprising: a pulse length scalable ferroelectric PZT material; and a power supply and associated circuitry arranged for excitation of the PZT material, wherein the excitation is characterized by an excitation (voltage) pulse length in the range of from 5 nanoseconds to 200 nanoseconds.

35. An FeRAM device, including a capacitor comprising a ferroelectric PZT material according to any one of claims 1 to 29.

36. The FeRAM device of claim 35, having a capacitor area of from about $10^4$ to about $10^{-2}$ $\mu m^2$.

37. A FeRAM device, including a capacitor comprising a ferroelectric PZT material according to any one of claims 1 to 29, and wherein the PZT material has a ferroelectric operating voltage below 2 Volts.

* * * * *